United States Patent [19]

Callaghan et al.

[11] Patent Number: 4,895,152

[45] Date of Patent: Jan. 23, 1990

[54] SYSTEM FOR CARDIAC PACING

[75] Inventors: Frank J. Callaghan, Miami; Edward A. Schroeppel, Miramar, both of Fla.

[73] Assignee: Telectronics N.V., Curacao, Netherlands Antilles

[21] Appl. No.: 219,806

[22] Filed: Jul. 14, 1988

Related U.S. Application Data

[63] Continuation of Ser. No. 823,610, Jan. 29, 1986, abandoned, which is a continuation-in-part of Ser. No. 807,547, Dec. 11, 1985, abandoned.

[51] Int. Cl.$^4$ ............................................. A61N 1/36
[52] U.S. Cl. ............................................. 128/419 PG
[58] Field of Search .................. 128/419 PO, 419 PT, 128/984, 786, 903

[56] References Cited

U.S. PATENT DOCUMENTS

| | | | |
|---|---|---|---|
| 3,949,758 | 4/1976 | Jirak | 128/419 PG |
| 4,114,627 | 9/1978 | Lewyn et al. | 128/419 PG |
| 4,378,020 | 3/1983 | Wappholz et al. | 128/419 PG |
| 4,387,717 | 6/1983 | Brownlee et al. | 128/419 PG |
| 4,399,818 | 8/1983 | Money | 128/419 PG |
| 4,466,448 | 8/1984 | Money et al. | 128/419 PG |
| 4,515,161 | 5/1985 | Wittkampf et al. | 128/419 PG |
| 4,558,702 | 12/1985 | Barreras et al. | 128/419 PG |
| 4,561,443 | 12/1985 | Hogrefe et al. | 128/419 PG |
| 4,579,119 | 4/1986 | Callaghan | 128/419 PG |
| 4,665,919 | 5/1987 | Mensine et al. | 128/419 PG |

FOREIGN PATENT DOCUMENTS

2119255  11/1983  United Kingdom .......... 128/419 PG

Primary Examiner—Francis Jaworski

[57] ABSTRACT

A system is provided for cardiac pacing, in which the output levels of the electrical stimulus pulses are responsive to the detection or non-detection of cardiac pacer evoked potentials. A pulse generator is provided for emitting electrical stimulus pulses at variable output levels. A pulse to pulse interval and an evoked response sensing period are provided. At the beginning of the pulse to pulse interval, an electrical stimulus having a first output level is emitted. If no evoked response is sensed during the sensing period, then an electrical stimulus at a selected maximum output level is emitted and, thereafter, the next electrical stimulus pulse is emitted at a second output level that is greater than the first output level. If a predetermined number of evoked responses are sensed during the sensing periods following the emission of stimulation pulses at other than the maximum output level, then the output level of the next electrical stimulus is decreased, but not to below a selected minimum output level.

7 Claims, 8 Drawing Sheets

SYSTEM FOR CARDIAC PACING

This application is a continuation of U.S. application Ser. No. 823,610, filed Jan. 29, 1986, and now abandoned which is a continuation-in-part of U.S. application Ser. No. 807,547, filed Dec. 11, 1985 now abandoned.

BACKGROUND OF THE INVENTION

An implantable cardiac pacer can have various pacing modes as well as various output parameters such as rate, output level (current or voltage, pulse duration or both), sensitivity, refractory period, etc. In some cardiac pacers both the mode, e.g. R-wave inhibited VVI, as well as the various output parameters, are preset during production, whereas in other cardiac pacers either mode or output parameters or both can be altered by external control or programming. Such output parameters and/or pacing mode changes are usually accomplished by the attending physician, usually during an office visit. Therefore, such cardiac pacers may not be responsive to the physiological requirements of the patients. Such requirements fluctuate often during a 24 hour period, certainly more frequently than the interval between patient's visits to the physician. Thus the patient must suffer less than optimum heart pacing.

Increased emphasis is being placed on the use of physiological parameters to control the output parameters, and particuarly the rate of stimulation, of implantable cardiac pacers. Such physiological parameters can include activity of the patient (Dahl, U.S. Pat. No. 4,140,132), sensed ionic changes (Wirtzfield, U.S. Pat. No. 4,202,339) and the stimulus-repolarization interval of the T-wave, (Rickards, U.S. Pat. No. 4,228,803). The detection of such changes is utilized either to increase or to decrease the rate of stimulation.

Measurement of physical activity or of the ionic level in the blood does not appear to measure the effectiveness of the pulse emitted from the cardiac pacer initiating myocardial contraction, nor do they permit analysis of the evoked potential, which is generated by the contracting heart. In addition, these do not consider the sympathetic and parasympathetic contributions to cardiac activity. However, measurements of the stimulus to T-wave intervals or repolarization potential does give an indication of effectiveness of stimulation. Absence of repolarization would indicate lack of stimulation; i.e. the heart failed to contract. However, the use of this repolarization to regulate output level (output current or voltage, output pulse duration, or both) could cause delay and irregularity in myocardial contraction or heart rate which the patient may feel.

Detection of the depolarization potential which must, by necessity, precede repolarization can give more immediate information on the presence or absence of effective stimulation within a sufficiently short period of time, to permit the resulting intervals between ventricular contractions to be made essentially equal by appropriate stimulating pulse generation.

In order to utilize the presence or absence of the depolarization potential or R-wave, to decrease (or increase) the output level of the cardiac pacer, one must detect the R-wave. When the same electrodes are used to generate pulses to stimulate muscle contraction and to record the resulting depolarization, the detected depolarization is markedly reduced, because it is masked or buried in the exponential decay of the polarization charge on the electrode resulting from the stimulus itself.

In Herscovici U.S. Pat. No. 4,543,956, issued Oct. 1, 1985, there is described a means for dissipating the polarization charge on the stimulating electrode. Stimulation and sensing of the resulting R-wave is accomplished by the same electrode. The polarization charge is dissipated by the use of a biphasic pulse in which the first phase is of shorter duration and greater amplitude, stimulating the myocardium. The second phase is of the opposite polarity, of lower amplitude and of longer duration than the first. When the polarization charge equals zero i.e. when no net charge is delivered, the second phase of the biphasic pulse drops to zero, and the evoked potential sensing amplifier is triggered into the "on" state.

The present invention pertains to a cardiac pacing system which preferably combines the unipolar and bipolar configuration. It typically uses a bipolar lead which may be placed in the atrium or the ventricle, or a pair of bipolar leads, one in the ventricle and one in the atrium for dual chamber pacing. The invention further pertains to a method of discrimination of the cardiac evoked potential from post stimulus electrode polarization. When the evoked potential is detected, its amplitude and/or configuration can be utilized to regulate automatically, with minimal external control, the implantable cardiac pacer's output characteristics. Thus the pacer itself can regulate the heartbeat in a more naturally physiological manner.

BRIEF DESCRIPTION OF THE INVENTION

In accordance with one embodiment of the present invention, a method of cardiac pacing is provided. In one embodiment, the method comprises the steps of (a) providing a pulse generator for emitting electrical stimulus pulses at variable output levels; (b) providing a pulse to pulse interval; (c) providing an evoked response sensing period; (d) emitting an electrical stimulus having a first output level at the beginning of the pulse to pulse interval, on a cardiac pacer lead that is positioned in a heart chamber to stimulate muscular contraction of the chamber; (e) sensing for an evoked response during the sensing period; (f) if no evoked response is sensed during the sensing period, then (1) emitting an electrical stimulus at a selected maximum output level, and (2) thereafter emitting the next electrical stimulus pulse at a second output level that is greater than the first output level.

In one embodiment, when the electrical stimulus is emitted the pulse to pulse and sensing intervals are reset to begin again. In one embodiment, if no evoked response is sensed during the sensing period, then also the next electrical stimulus pulse, after the maximum output level stimulus, is emitted at a second output level that is greater than the first output level. If a predetermined number of evoked responses are sensed during the sensing periods following the emission of stimulation pulses at other than the maximum output level, then the output level of the next electrical stimulus is decreased but not to below a selected minimum output level.

In one embodiment of the invention, an alert period is provided and the system senses for a natural heartbeat during the alert period. If a natural heartbeat is detected during the alert period, then the emission of the stimulating pulse is inhibited and the pulse to pulse interval and sensing periods are reset.

In one embodiment of the invention, the system determines whether the activity sensed during the evoked response sensing period is an evoked response or is a natural heartbeat. The determining step comprises the step of determining the time interval between the emission of the electrical stimulus and the sensing of the activity during the evoked response sensing period for a plurality of cycles. If the time is equal for the plurality of cycles, then the activity is an evoked response.

In accordance with the present invention, an apparatus is provided for performing the steps described above. To this end, a pulse generator is provided for emitting electrical stimulus pulses at variable output levels. A pulse to pulse interval and an evoked response sensing period is provided. The pulse generator is operable to emit an electrical stimulus having a first output level at the beginning of the pulse to pulse interval. Means are provided for sensing for an evoked response during the sensing period. Means are provided for emitting an electrical stimulus at a selected maximum output level if no evoked response is sensed during the sensing period. In addition, means are provided for emitting the next electrical stimulus pulse at a second output level that is greater than the first output level if no evoked response is sensed during the sensing period.

On the other hand, means are provided for decreasing the output level of the next electrical stimulus but not to below a selected minimum output level if a predetermined number of evoked responses are sensed during the sensing periods following the emission of the pulses at other than the maximum output level.

A more detailed explanation of the invention is provided in the following description and claims, and is illustrated in the accompanying drawings.

DESCRIPTION OF SPECIFIC EMBODIMENTS

Figure 1:
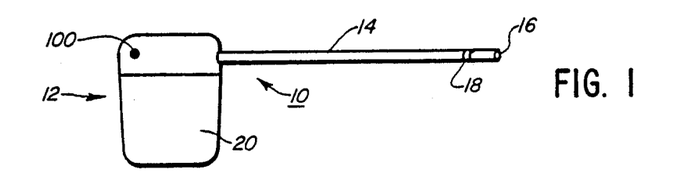
FIG. 1 is an elevational view of a cardiac pacing system with a bipolar lead which functions both as a unipolar and a bipolar system at different steps of the operating cycle.

Referring to the drawings, in FIG. 1 a single chamber cardiac pacing system 10 includes pulse generator 12, which may be of generally conventional electronics except as otherwise described herein. Pervenous bipolar lead 14 is also provided and may be of conventional bipolar pervenous or epicardial design.

First electrode 16 may be a porous, platinum-iridium, hemispherically shaped electrode on the distal end of lead 14, communicating with a metal conductor inside of the lead. Ring electrode 18 serves as a second electrode, being capable of electrical isolation by means of the circuitry and pulse generator 12 from first electrode 16, and being typically spaced at least 0.5 cm. from first electrode 16. Second, ring shaped electrode 18 may be also made of the same alloy and may communicate with its own circuit wire within lead 14, and may or may not be porous-coated.

The circuitry of pulse generator 12 may be sealed in a hermetic container, for example titanium can 20, as shown.

Cardiac pacing system 10 may be external or surgically installed into the patient, and may operate to pace the patient's heart as follows.

When the pacer can 20 is treated as an independent electrode, the single chamber cardiac pacing system 10 carries three electrodes; can 20, first electrode 16, and second electrode 18. The operation of the pacing system as described applies to both the atrial and ventricular leads of a dual chamber cardiac pacer or an atrial standby pacer. However, for purposes of simplicity of disclosure, the details of operation will be described for a ventricular asynchronous pacer (VOO) or a ventricular inhibited demand pacer (VVI).

A pacing cycle begins when a physiologic electric stimulus is emitted from first electrode 16 to stimulate muscular contraction of at least a portion of the heart. The stimulus is of a magnitude and duration which is not harmful to the heart and which is well known to those skilled in the art to evoke a contraction response from the heart muscle. The pulse of electric stimulus 30 is graphed in FIG. 4 at channel A, having a typical duration of 0.1 to 2 milliseconds.

Figure 5:
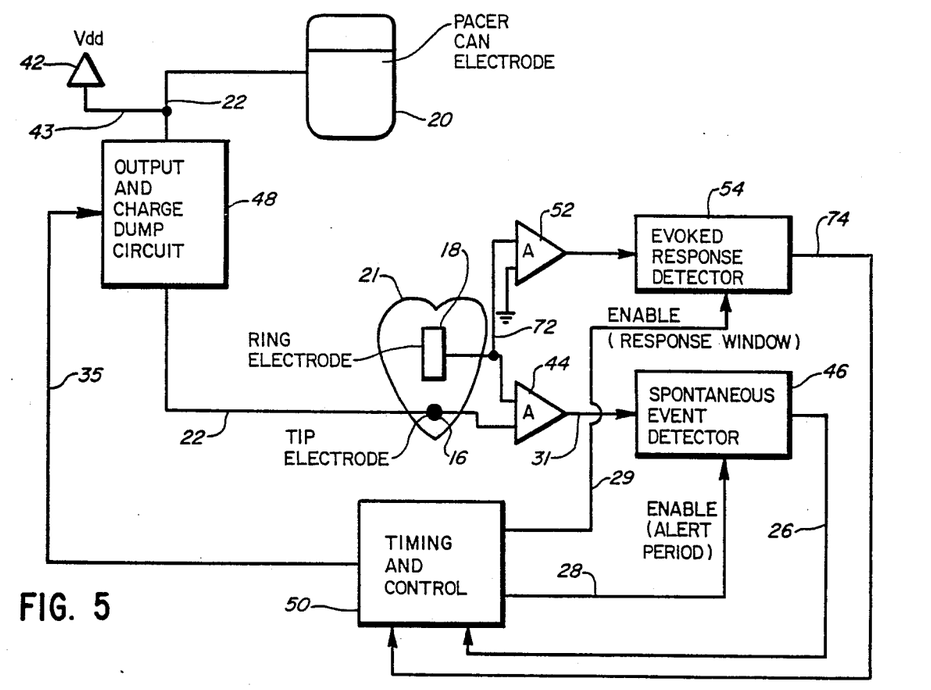
FIG. 5 is a schematic block diagram of a single chamber cardiac pacer with evoked potential monitoring in accordance with this invention.

Referring to the circuit of FIG. 5, pacer can 20 is shown serving as a reference electrode for electrodes 16, 18, carried at the heart 21 which is shown in schematic manner. Stimulus 30 passes through conductor 22 to be emitted from tip electrode 16. The naturally occurring cardiac electrical activity is amplified by amplifier 44 and transmitted via line 31 to a spontaneous event detector 46 to begin a timing process. The signal proceeds via conductor 26 into timing and control circuitry module 50 which, in turn, has feedback and control wires 28, 29 connected, respectively, to detector 46 and to evoked response detector 54. Likewise an output from timing and control circuit 50 is connected via line 35 to output and charge dump circuit 48.

Figure 4:
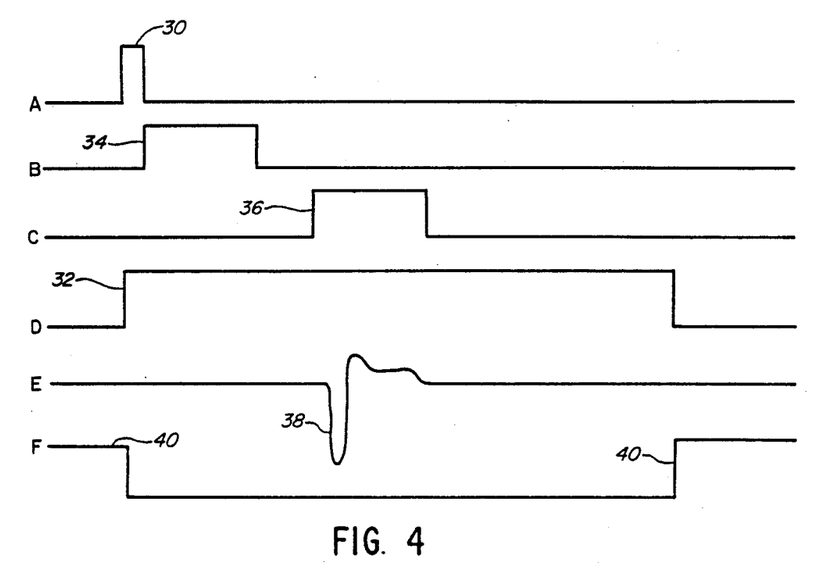
FIG. 4 is a timing diagram of the relationship of the electronic events which take place during a single cycle in accordance with this invention.
Figure 6:
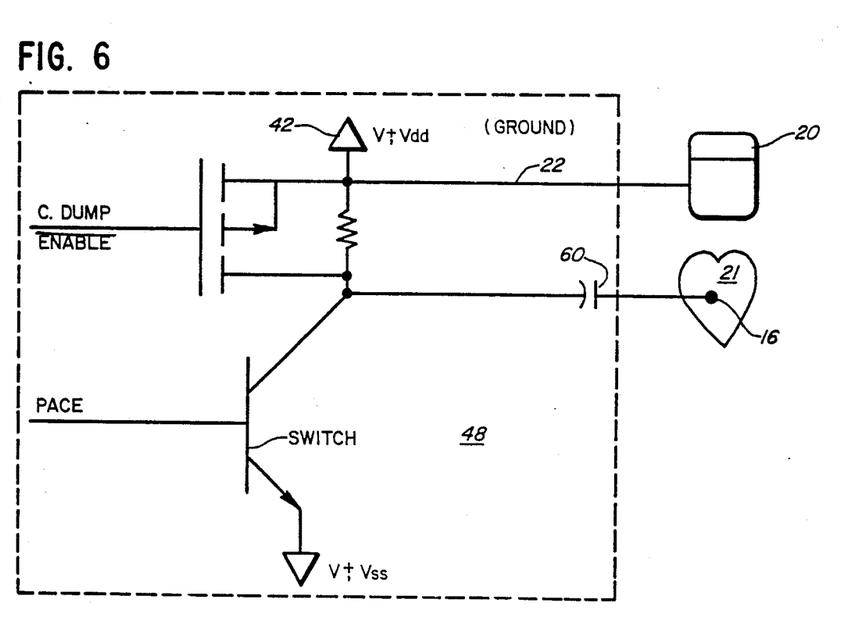
FIG. 6 is a schematic block diagram of the charge dump circuit used in the device of FIG. 6.

Immediately following the emission of pulse 30 from electrode 16, charge dump circuit 48 is activated, with the charge dump pulse 34 being illustrated on channel B of FIG. 4, the duration of the charge dump being about 5 to 15 milliseconds. The charge dump may be provided using a conventional charge dump circuit 48 such as illustrated in FIG. 6. During the charge dump period, the electrical charge on output coupling capacitor 60 (FIG. 6) and first electrode 16 are discharged through the heart 21. Thus the post-stimulus polarization potential of electrode 16 is quickly diminished.

Evoked response detector 54 is then activated by timing and control circuit 50 through conductor 29. A window of time 36 is opened as illustrated in channel C of FIG. 4, its duration being typically 10 to 50 milliseconds. It is only during this time that evoked response detector 54 is activated to detect an evoked electrical response coming from the heart and to indicate a contractile response to the physiological pulse of electric potential 30.

The stimulus from electrode 16 can be seen to be in the unipolar mode. Likewise, detection of the evoked response is unipolar, being detected by electrode 18, which communicates through conductor 72 to amplifier 52, which sends the amplified signal to detector 54. When an evoked response is detected, detector 54 may signal timing and control circuitry 50 through line 74 for further timing of the system.

It is noted that the window of time 36 on channel C of FIG. 4 is positioned in a block of time 32 (channel D of FIG. 4) which generally represents a refractory period in which first electrode 16 may not be used to sense any electrical activity. By this invention, it can be seen that the evoked response can be detected during such a refractory period.

Channel E in FIG. 4 shows the evoked cardiac electrical activity 38 within evoked response detection period 36, and which is detected by second electrode 18. It can be seen that the detection of evoked heartbeat response 38 is detected by second electrode 18 in the unipolar mode. The detected evoked response is sent through conductor 74 to timing and control circuit 50, and may serve to set the timer to zero for timing the next physiological pulse to be emitted from first electrode 16.

However, there is a need to determine that natural heartbeats will not show up at unexpected times, to avoid the result where the pacing system disrupts and interferes with the natural heartbeat. To this end, beginning essentially at the end of refractory period 32, during which event detector 46 is disabled from sensing electric pulses, an alert period 40 is provided to monitor a naturally occurring cardiac electrical activity until such time as the next pulse 30 is sent out through first electrode 16. Alert circuitry 46 may be activated and shut down by timing and control circuit 50 through conductor 28. When the alert phase 40 is in operation, both electrodes 16 and 18 are operating together in a bipolar mode, with both electrodes communicating with amplifier 44, which in turn is connected to spontaneous event detector 46.

In the event of a spontaneous heartbeat, a signal may be sent from spontaneous event detector 46 via line 26 to timing and control circuit 50, to cause the electronics to recycle from any time in the cycle to the beginning of the cycle, without generation of an electric pulse 30 from first electrode 16. Every time natural cardiac electrical activity takes place during alert period 40, no electric pulse 30 will be generated.

In the event, however, that detector 46 does not detect natural cardiac electrical activity during the alert period, timing and control circuitry will cause another electric pulse 30 to be generated via electrode 16.

Figure 7:
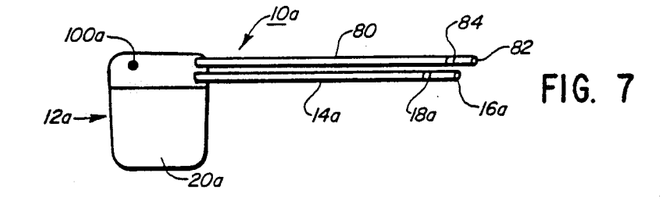
FIG. 7 is an elevational view of a dual chamber pacing system, each chamber having a bipolar lead, each bipolar lead functioning both as a unipolar and a bipolar system at different phases of the cycle of operation.

Turning to FIG. 7, a cardiac pacer system 10a is provided, having pacer circuitry 12a enclosed in a metal can 20a of the type similar to FIG. 1. Pacer lead 14a carries similar electrodes 16a, 18a, similar to the electrodes of the previous embodiment.

However, an additional pacer lead 80 is provided, carrying first electrode 82 and second electrode 84 similar to first and second electrodes 16, 18, or electrodes 16a, 18a. Lead 14a may be positioned in a ventricle of a heart, while lead 80 is positioned in the atrium.

The functioning of the individual leads 14a, 80 of pacer 10a is closely analogous to the functioning of lead 14 and its electrodes in the embodiment of FIG. 1, with the same steps being used for providing the electric pulse via either of electrodes 16a, 82, sensing the evoked response with second electrodes 18a, 84 within a predetermined time window, and then timing the next electric pulse from first electrodes 16a, 82 from the evoked response, unless, during an alert period where the respective first and second electrodes are operating together in bipolar mode, an electric signal of a natural heartbeat is detected.

The charge dump circuit 48 may be used with each of the leads of this second embodiment, in a manner similar to its optional use in the first embodiment. Such a charge dump on the electrode alleviates the cathodal polarization on that electrode to avoid a "near field" signal to the second electrode. In other words, the second electrode, relative to the can 20 or 20a, operating as a reference electrode, can detect the polarization of the tip, which can decrease the evoked response signal when no charge dump occurs.

Furthermore, when can 20, 20a is used as a reference electrode, it has large surface area, low stimulation current density, and low post-stimulus polarization potential. The pacer can serves as the anode at Vdd and is a reference for the unipolar single ended amplifier. The cardiac pacer can 20, 20a may be connected to the positive side of the battery.

Because second electrodes 18, 18a, 84 are slightly removed from the pulse site of the first electrodes, there is a physiological propagation delay between stimulation and the arrival of the cardiac excitation wave front at each second electrode. This delay allows more time for the polarization recovery of the second electrode, as needed, dependent upon the magnitude of the pulse, the distance between the first and second electrodes, and the myocardial conduction velocity.

Figure 2:
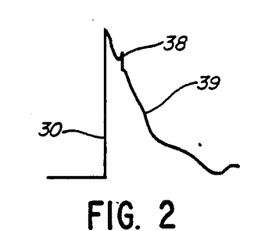
FIG. 2 is a diagram showing how the evoked potential may be masked by exponential decay of the pacer pulse when one attempts to sense the evoked potential from the electrode which emits the pacer pulse.

Referring now to FIG. 2, an electrographic tracing of the physiologic pulse provided by the first electrode is shown, in which the evoked response 38 is attempted to be monitored from a first electrode. It can be seen that the evoked response 38 is barely visible, being masked by the exponential decay 39 of the polarization of the first electrode.

Figure 3:
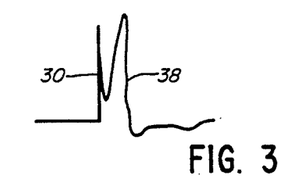
FIG. 3 is a diagram of the evoked potential as it may be detected in accordance with this invention.

Now, turning to FIG. 3, this electrogram is taken from the second electrode in accordance with this invention. Stimulus pulse 30 is shown, and a second pulse 38 is shown, which is the evoked response. Thus it can be seen that an evoked response can be detected with great ease in accordance with this invention.

Hence, a cardiac pacing system is provided, which functions during its cycle as both a bipolar and a unipolar system depending upon a particular moment-by-moment function in the cycle. In the bipolar mode, when electrical activity indicative of naturally-occurring cardiac activity is being sensed, the system exhibits good immunity from electromagnetic interference, freedom from myopotential inhibition, good rejection of far-field cardiac events, good rejection of post-stimulus polarization potentials, and true differential sensing with a remote reference.

However, in the unipolar mode, such as during the time of stimulation 30, the surface electrocardiographic interpretation is easier due to a prominent unipolar stimulus artifact. Likewise, anodal cross-stimulation is avoided and there is no need for isolated output stages.

Finally, the use of the second ring electrode 18, 18a, 84 in unipolar mode can be used with a charge dump on the first electrode if needed to reduce polarization of the second ring electrode to a sufficient degree for good sensing of an evoked response. Likewise the system works with available linear bipolar electrodes, so that no design change from currently available bipolar cardiac leads is required. Verification of capture on a beat-by-beat basis is provided, with a wide safety margin. One may also determine if an exit block occurs at the stimulation site with automatic control of the stimulus parameter via capture search and threshold tracking circuitry. Likewise, the apparatus of this invention enables a rate response function which is based on the ventricular evoked response. Thus the heart rate may be controlled in a manner which is natural and desirable.

If desired, a separate electrode 100, 100a may be used as the reference electrode anode in either of the pacer systems 10, 10a rather than the metal cans 20, 20a. Such a reference electrode may also be an additional ring on lead 14, if desired.

Figure 8:
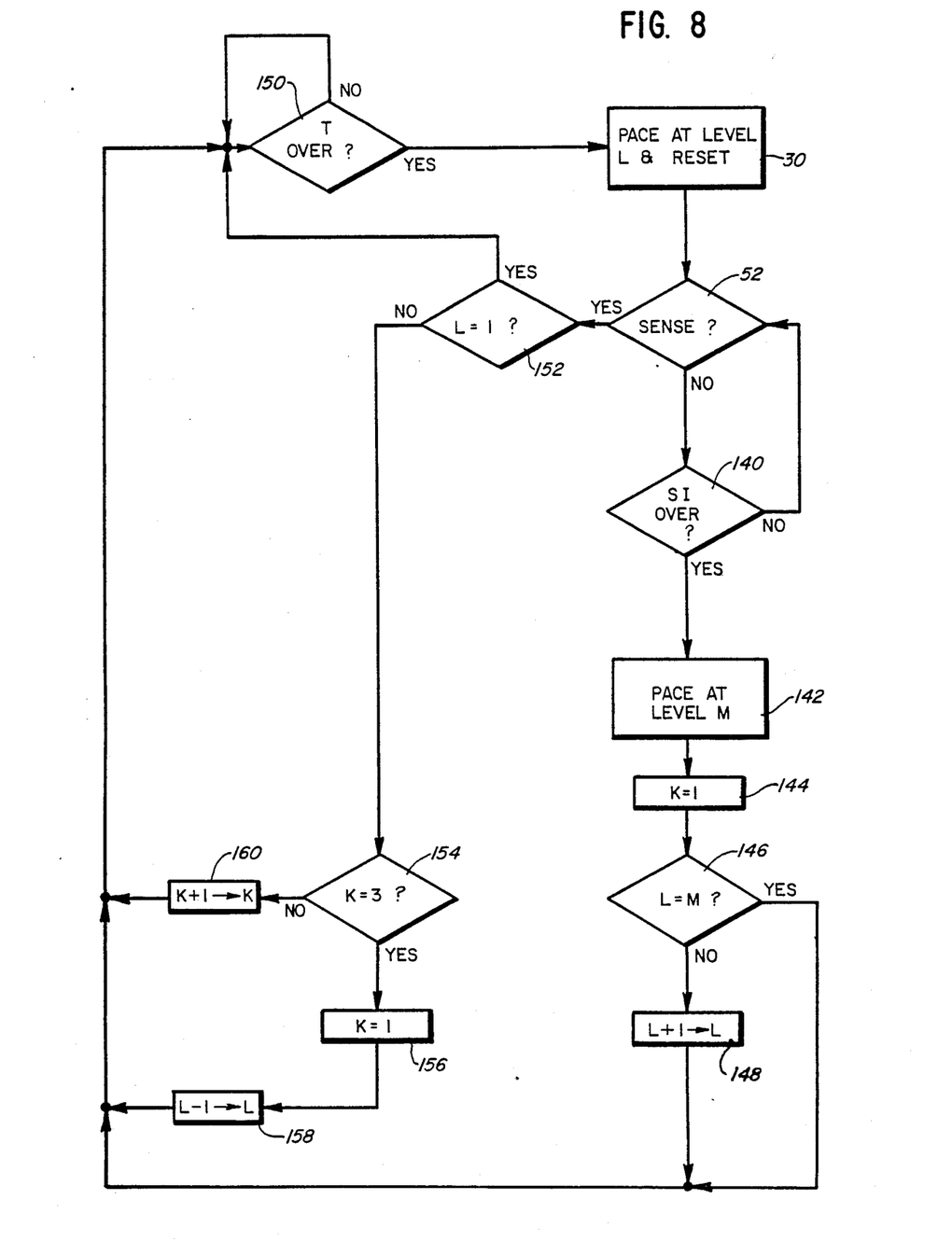
FIGS. 8, 9, and 10 are flow charts, showing three different ways in which the invention of this application may be utilized in a computer-aided process.

FIG. 8 is a flow chart showing pacer operation in one embodiment whereby the detected evoked response is utilized to control output. Pacer 12 emits an output pulse 30 from electrode 16 (FIG. 1). Output pulse 30 activates the evoked response sensing amplifier 52 (FIG. 5) for a sensing interval of typically less than 50 milliseconds (140 - FIG. 8). At the end of the sensing interval, if no evoked response was detected, the cardiac pacer emits a stimulus at the maximum output level (142), and the pulse to pulse interval is reset. The counter is set to 1 (144).

Furthermore, if the output level is not at its maximum level (146), the existing output level is increased to its next higher output level $L+1 \rightarrow L(148)$. When the pulse to pulse interval T is complete, or the programmed duration of the pulse to pulse interval is complete, the cardiac pacer emits another pulse 30 from first electrode 16 at the output level as determined by logic units 146 or 148.

Again, the evoked response detector 54 is activated to detect evoked response 38. If the output level is at its lowest value L=1(152) nothing further is needed, and the pulse to pulse interval elapses (150). However, if the output level is not at its lowest value and there has been a total of three (or any other predetermined number) detected evoked responses (154) at that particular output level, the counter is reset to 1 (156), and the output level is decreased to the next lower level (158).

At the end of the programmed pulse to pulse interval (150), the cardiac pacer will stimulate the heart at the output level determined at 152 or 158. If, on the other hand, three evoked responses (or any predetermined number) have not been detected, counter (160) is incremented by 1, and the pulse-to-pulse timing continues.

Figure 9:
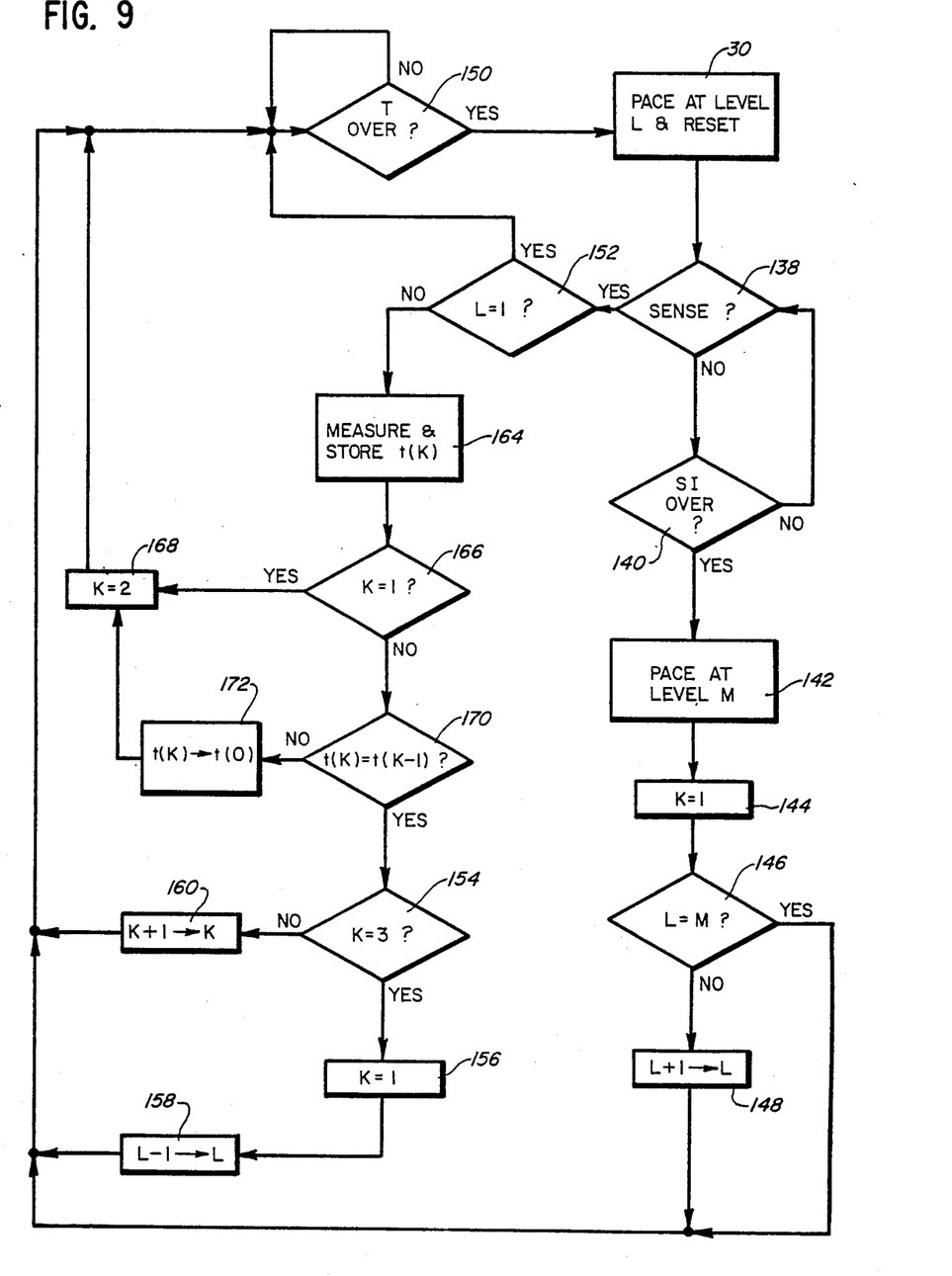

Referring now to FIG. 9, a second flow chart is disclosed showing the pacer operation of another embodiment. It can be seen that many of the steps are the same as in the previous embodiment of FIG. 8, the same steps carrying the same reference numerals; specifically, reference numerals 130 through 152 and reference numerals 154–160.

The added steps in FIG. 9 are based on the premise that evoked responses to each stimulus occur at approximately equal intervals after stimulus, whereas in a non-evoked potential from natural cardiac action, this interval tends to be more variable. Further, the output level (30) is changed after three evoked potentials have been detected in the sensing interval of the evoked response amplifier.

The system determines (152) whether or not the output level is at its lowest programmed value. If it is not, the time interval t(k) is measured and stored (164). This time interval is a measured time within the less than 50 milliseconds in which the evoked potential may be detected.

Counter 166, if set at 1, proceeds to signal counter 168 to increment k to equal 2, and in this case the process proceeds to the end of the programmed pulse-to-pulse interval, this being monitored (150) to determine the end of such interval.

However, if counter 166 is not at 1, the interval sensed is compared to the prior sensed interval (170). If the two intervals are equal within a predetermined error range, and counter 154 is at 3, then the series proceeds in the manner described in the previous embodiment of FIG. 8. However, if the interval sensed is not equal within predetermined limits, (i.e., natural heartbeats are detected), then t(k) replaces t(O) (172), and counter 168 is made to equal 2, and the series proceeds as described in the previous embodiment of FIG. 8. By making counter 168 equal 2, the counter will not reach 3 if these are natural heartbeats, and the output level of the stimulating pulse will not decrease.

If, however, the two compared times (170) are equal, and k=3 as determined at point 154, then k is made to equal 1 at point 156; and the output level L is reduced by one unit (158) for the next emitted pulse 30 as timed at timing circuit 150.

Figure 10:
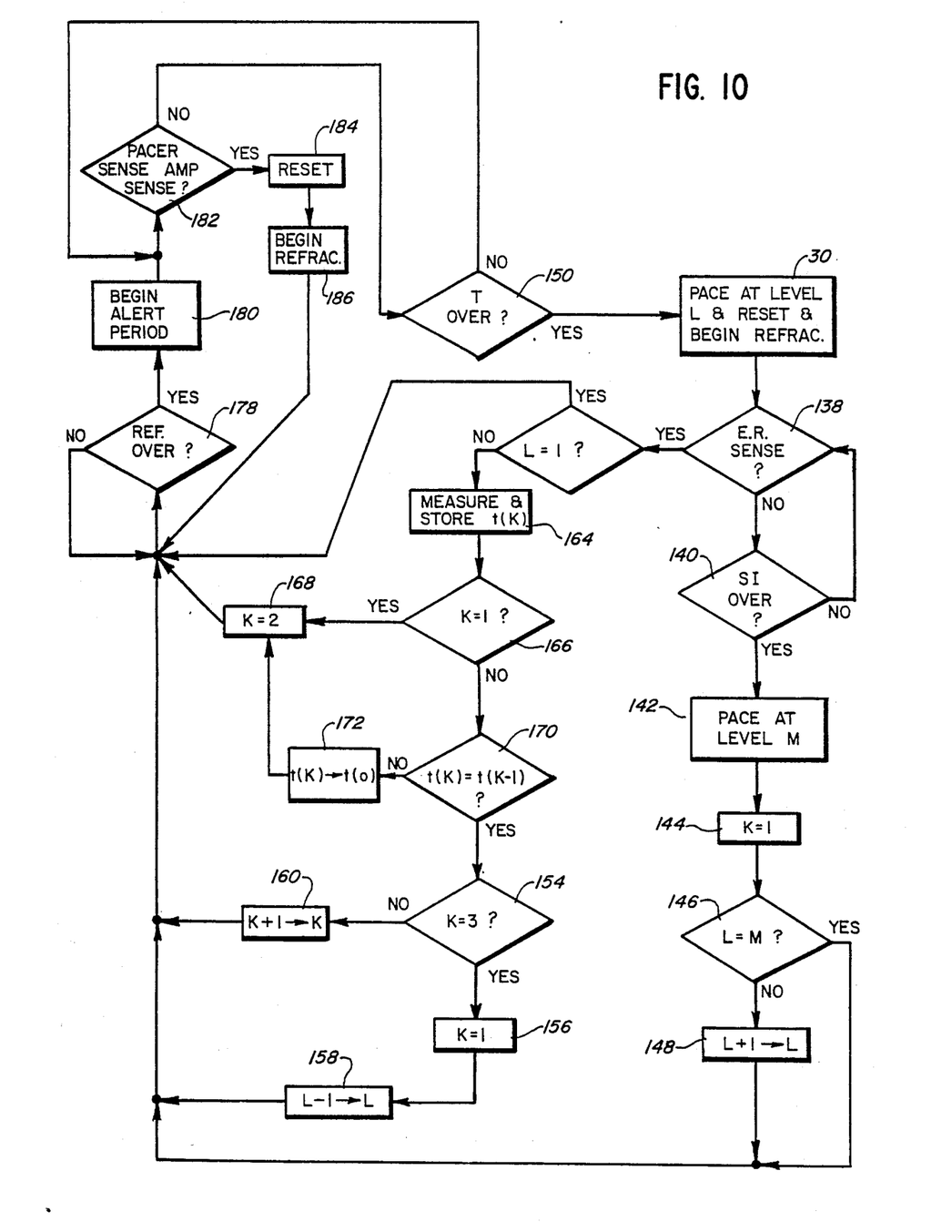

Turning to FIG. 10, it can be seen that the functions of FIG. 9 are still present, bearing the same reference numerals, but that added functions are also provided.

Basically, a pacing sensing amplifier 182 is added to the circuit so that naturally occurring electrical activity can be detected (VVI). In this system, the pulse-to-pulse interval is divided into a refractory period (186) and an alert period (180). The refractory period is the time that first electrode 16 cannot sense electric signals from the heart. The alert period is the time when naturally occurring electrical activity is sensed.

The heart electrical activity, when sensed during the alert period, initiates a new pulse-to-pulse interval.

The delivery of pulse 30 is unipolar. The sensing of the evoked ventricular activity is unipolar i.e. between the ring electrode 18 and the metal case 20 of the cardiac pacer, for example. However, the sensing of naturally occurring ventricular activity is preferably bipolar, i.e. between the tip electrode 16 and the ring electrode 18.

In the FIG. 10 system, two different electrical events are being sensed; that which results from pulse 30, such evoked response occurring almost immediately after the pulse, and also that electrical activity which can occur by a non-induced heartbeat.

The system which detects the evoked response is the same as the previous embodiment. To this system are added steps to detect the electrical activity of spontaneous heart activity.

Pulse 30 activates the evoked response sensing amplifier and detector 52, 54 (FIG. 5) and naturally sets off the refractory period 32 (FIG. 4). The system determines the end of the refractory period (178). At the end of the refractory period, alert period 180 begins, at which time the sensing for spontaneous heart activity takes place. If such activity is sensed by amplifier 182, the programmed pulse-to-pulse interval is reset to zero (184), and the refractory period begins again (186). However, if no spontaneous activity is sensed (182) during the alert period, the timing completes its programmed interval (150), and another output pulse 30 is emitted from electrode 16, resetting the sensing interval for the evoked response and the refractory period.

Figure 11:
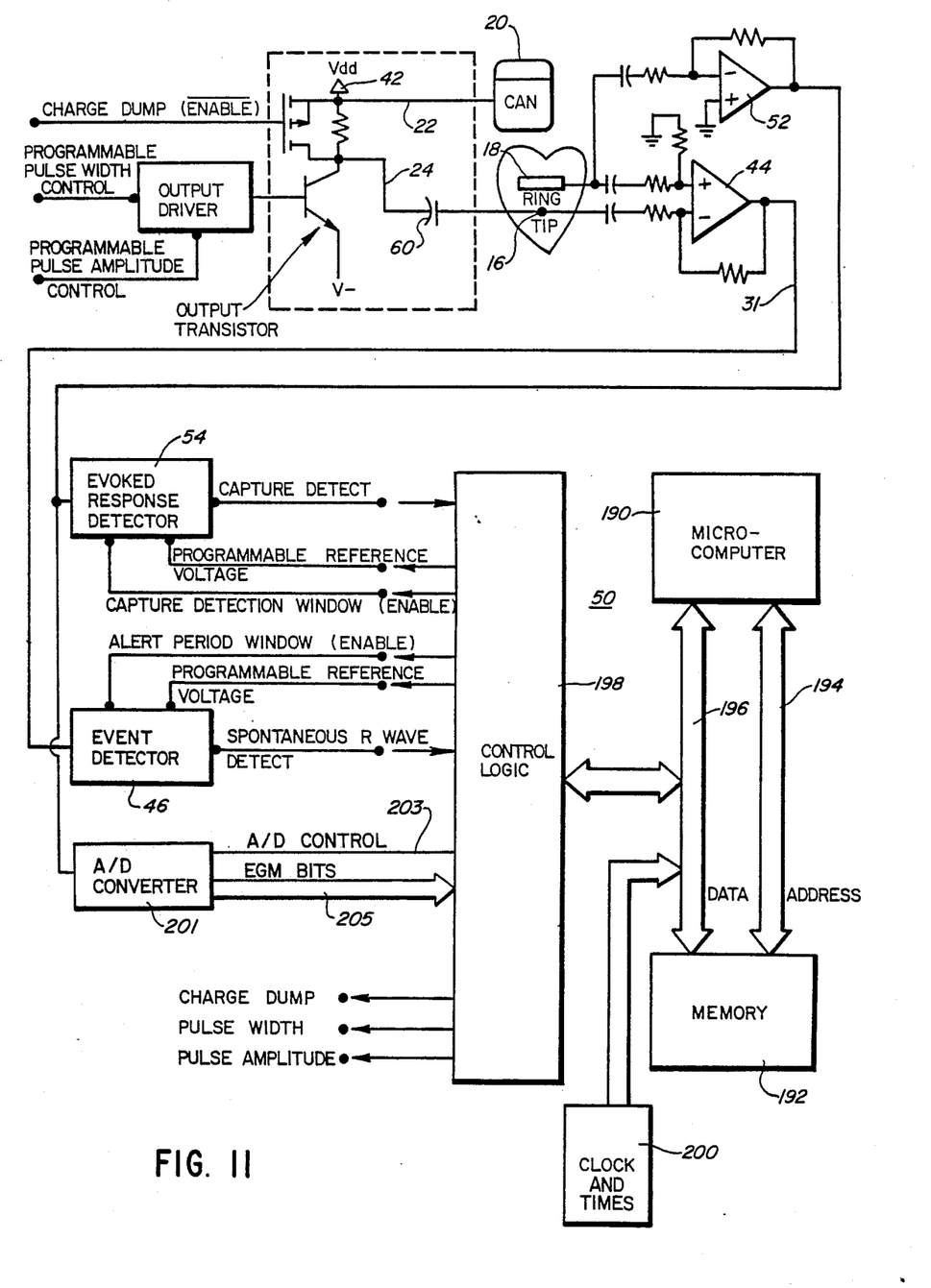
FIG. 11 is a schematic diagram of another embodiment of a pacer system constructed in accordance with the present invention.

A relatively detailed schematic diagram of the pacer electronics is presented as FIG. 11. Referring to FIG. 11, it is seen that the same reference numerals are used for the same components of FIG. 5. Timing and control circuit 50 comprises a microcomputer 190 which addresses a memory 192 via address bus 194. Data bus 196 is coupled between microcomputer 190 and memory 192, and conventional control logic 198 is coupled to data bus 196. A crystal controlled clock 200 is used for providing appropriate clock pulses for the system. The functions of the control logic inputs and outputs are designated on FIG. 11.

The intracardiac electrogram signals (EGMs) may be telemetered out immediately for analysis or may be stored for future use and telemetered out subsequently for analysis. To this end, still referring to FIG. 11, ring 18 is constantly monitored for EGMs. These signals are linearly amplified by amplifier 52. Control logic 198 determines at which times it is appropriate to store the digitized EGM. This may be determined by a clock within the pacer or be triggered by detection of a specific cardiac event using recognition means or by the patient himself.

In addition to the output of amplifier 52 being connected to the input of evoked response detector 54, the output of amplifier 52 is also connected to the input of an analog to digital converter 201. Control line 203 from control logic 198 turns on the A to D converter 201 and digitizes the signal. These bits are stored in memory 192 via data lines 205 and 196. To these data may be added some bits (from microcomputer 190) to indicate the time of occurrence of the stored EGM.

Alternatively, A to D converter 201 may always be in operation and the digitized EGM constantly being stored so that, upon occurrence of the trigger mentioned above, a predetermined number of seconds of EGM occurring prior to the trigger may be retained.

At a later time, all stored EGM sequences may be read out of memory when requested by personnel using a Pacer Programmer. EGM data is passed via bus 196 to a telemetry system via 207. Upon reception by the programmer, they are converted to analog form and then may be observed on a recording device.

Real time observation of the EGM, unobscured by electrode polarization potentials, may be obtained by sensing at ring 18, linearly amplifying the EGM by amplifier 52, digitizing by A to D converter 201, and transmitting the data bits via line 205 and line 196 to telemetry system 207. This may occur upon request of an external Pacer Programmer. Alternatively, the EGM obtained by sensing at ring 18 may be directly telemetered to an external receiver without digitizing the amplified EGM, for example by using a telemetering system such as disclosed in William P. Batina and Lamar H. Gipson U.S. Pat. No. 4,562,840, issued Jan. 7, 1986, assigned to Cordis Corporation.

Figure 12A:
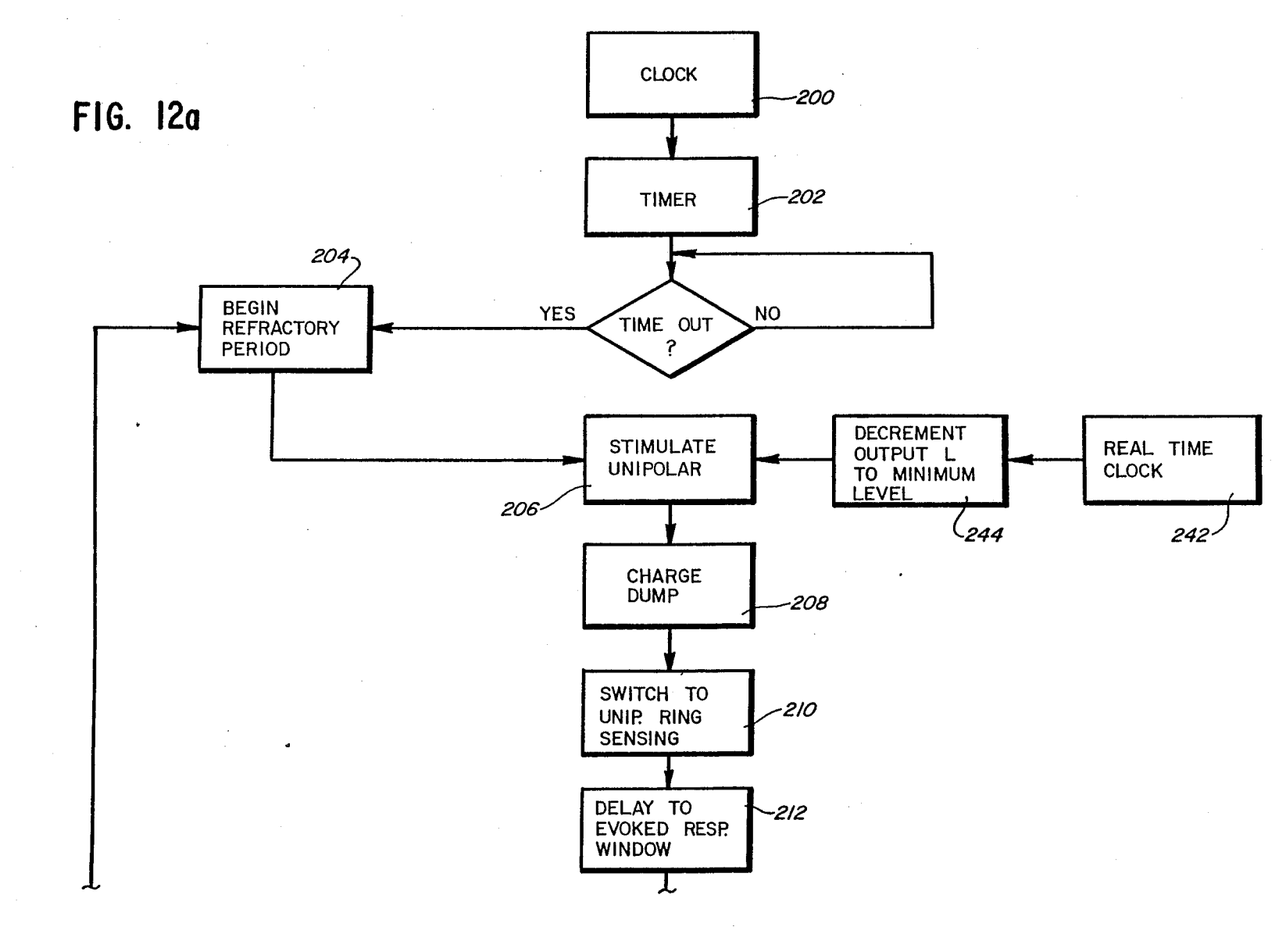
FIGS. 12A–12B, when connected together, comprise a flow chart depicting an operation of the diagram of FIG. 11.
Figure 12B:
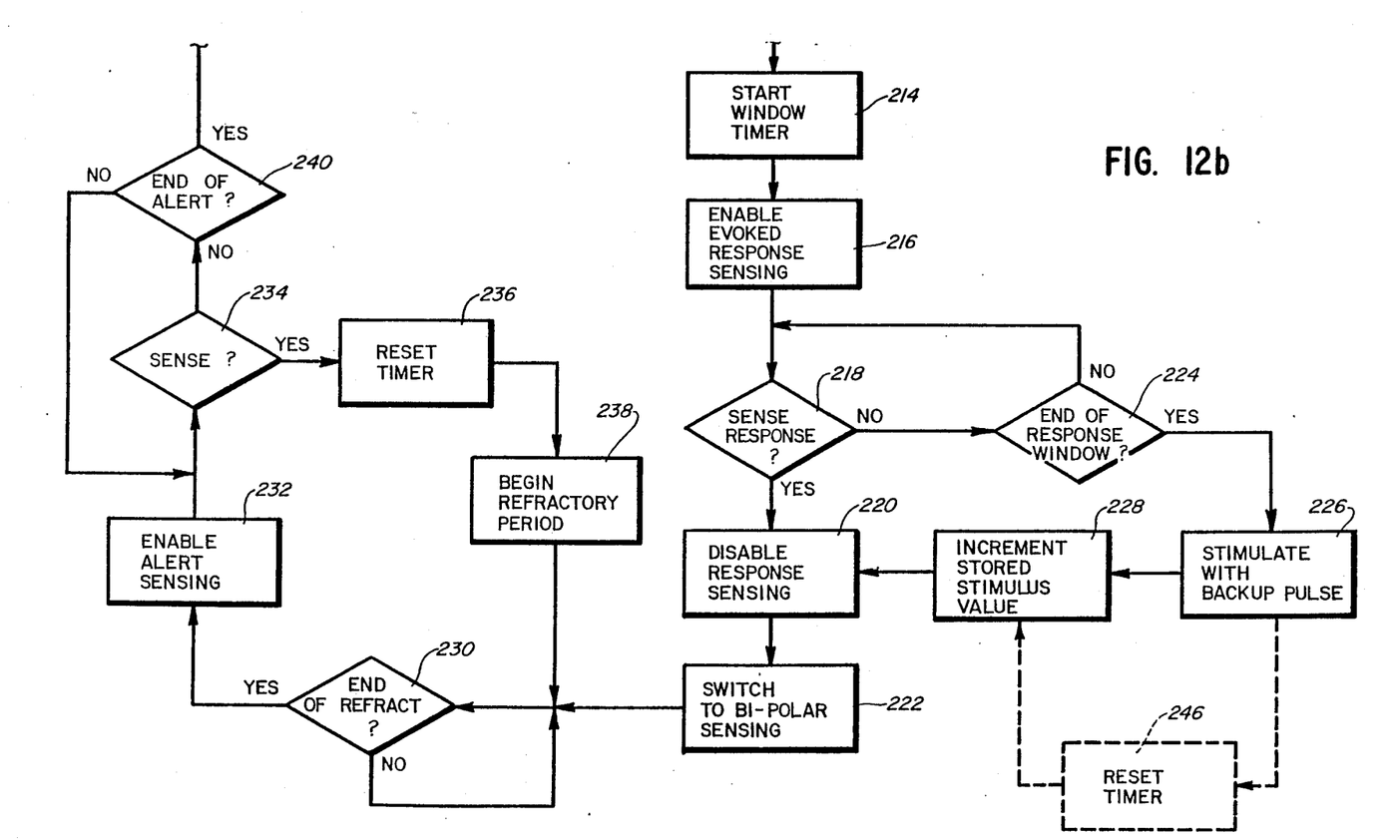

A flow chart illustrating an operation of the circuit of FIG. 11 is presented as FIGS. 12A–12B.

Referring to FIGS. 12A and 12B, the operation of the system is as follows. Clock 200 will operate timer 202 which, when timed out, will begin a refractory period 204 and issue a stimulation pulse in a unipolar manner 206. Charge dump will occur 208 and the system will switch to unipolar ring sensing 210. A delay will occur to the evoked response window 212, and the window timer will then begin 214. Evoked response sensing will be enabled 216. If an evoked response is sensed 218, the response sensing will then be disabled 220 and the system will switch to bipolar sensing 222. On the other hand, if an evoked response is not sensed 218, the system will determine if the response window has ended 224, and once the window has ended without sensing a response, a stimulating backup pulse 226 will issue. The stored stimulus value will then be incremented 228. The response sensing will then be disabled 220, and the system will switch to bipolar sensing 222.

Once this system switches to bipolar sensing 222, the system will determine if the refractory period has ended 230. If the refractory period has ended, the alert sensing will be enabled 232. The system will sense for a natural R wave 234, and if an R wave is sensed, the timer will be reset 236, and a new refractory period will begin 238. If an R wave is not sensed by the end of the alert sensing period 240, a new refractory period will begin 204, and a stimulation will issue in a unipolar manner 206.

The stimulation pulse which is issued in the unipolar manner 206 is also controlled by a real time clock 242 which decrements the output level L to a minimum level 244 at selected intervals. The selected intervals could be any selected amount of time, perhaps every twelve hours, or every hour, or every fifteen minutes, etc. At these selected intervals, if an evoked potential is not sensed in response to the lowest level of stimulation, a stimulus at the highest output level M occurs. The stored (now lowest level of) output stimulation is then incremented to the next highest level, and should this incremented output level not evoke a response at the next cycle, the output stimulus level is again incremented.

It is preferred that the timer be reset every time a stimulation backup pulse is issued 226. If the timer were not reset, every time a stimulation pulse at a maximum level is issued there will be a variation in the interval between stimuli as read by the cardiologist on an ECG. If the timer is reset 246, after each stimulation with a backup pulse 226, the interval between the maximum output stimulus and the subsequent stimuli will remain constant.

The above has been offered for illustrative purposes only, and is not intended to limit the scope of the invention of this application, which is as defined in the claims below.

What is claimed is:

1. The method of cardiac pacing and sensing which comprises the steps of:
   providing a pulse generator for emitting an electrical stimulus;
   providing a cardiac pacing lead for connection to said pulse generator and having a first electrode at its distal end and a spaced, second electrode free of electrical connection to said first electrode;
   providing an output capacitor;

positioning said lead in a heart chamber;

periodically emitting an electrical stimulus having a first polarity from said first electrode to stimulate cardiac contraction;

discharging an electrical charge, having a polarity that is opposite to the first polarity of the electrical stimulus, from said output capacitor through the heart muscle via said first electrode immediately following the emission of said electrical stimulus, whereby the post stimulation potential of said first electrode is reduced and sensing of an evoked response is enhanced;

thereafter sensing said evoked response by said second electrode carried by said lead and spaced from said first electrode and free of electrical connection thereto; and transmitting said sensed evoked response to a point of use.

2. A method as described in claim 1, including the steps of providing telemetering means, digitizing the sensed response, storing the digitized response, and transmitting the stored digitized response, upon command of a programmer, to said telemetering means for observing the stored response externally.

3. The method of cardiac pacing and sensing which comprises the steps of:

providing a pulse generator for emitting an electrical stimulus;

providing a cardiac pacing lead for connection to said pulse generator and having a tip electrode at its distal tip and a spaced ring electrode free of electrical connection to said tip electrode;

providing an output capacitor;

positioning said lead in a heart chamber;

periodically emitting an electrical stimulus having a first polarity from said tip electrode carried on the distal tip of said lead to stimulate cardiac contraction;

discharging an electrical charge, having a polarity that is opposite to the first polarity of the electrical stimulus, from said output capacitor through the heart muscle via said first electrode immediately following the emission of said electrical stimulus, whereby the post stimulation potential of said first electrode is reduced and sensing of an evoked response is enhanced;

thereafter detecting an electric potential response evoked by said stimulus pulse, indicating said muscular contraction, by a ring electrode carried by said lead and spaced from said tip electrode and free of electrical connection thereto; and transmitting said digital response to a point of use.

4. A method as described in claim 3, including the steps of providing telemetering means, digitizing the sensed response, storing the digitized response, and transmitting the stored digitized electric potential response, upon command of a programmer, to said telemetering means for observing the stored electric potential response externally.

5. The method of cardiac pacing and sensing which comprises the steps of:

providing a pulse generator for emitting an electrical stimulus;

providing a cardiac pacing lead for connection to said pulse generator and having a tip electrode at its distal tip and a spaced ring electrode free of electrical connection to said tip electrode;

providing an output capacitor;

positioning said lead in a heart chamber;

periodically emitting an electrical stimulus having a first polarity from said tip electrode carried on the distal tip of said lead to stimulate cardiac contraction;

discharging an electrical charge, having a polarity that is opposite to the first polarity of the electrical stimulus, from said output capacitor through the heart muscle via said tip electrode immediately following the emission of said electrical stimulus, whereby the post stimulation potential of said first electrode is reduced and sensing of an evoked response is enhanced;

thereafter detecting an electric potential response evoked by said pulse, indicating said muscular contraction, by said ring electrode; and telemetering the detected electric potential response to an external receiver.

6. Apparatus for cardiac pacing and sensing, which comprises;

a cardiac pacing lead having a tip electrode on its distal end and a ring electrode spaced from said tip electrode;

said cardiac pacing lead being adapted for positioning within a heart chamber;

an output capacitor coupled to said tip electrode;

means for transmitting to said tip electrode an electrical stimulus having a first polarity to stimulate cardiac contraction;

means for discharging an electrical charge, having a polarity that is opposite to the first polarity of the electrical stimulus, from said output capacitor through the heart muscle via said first electrode immediately following the emission of said electrical stimulus, whereby the post stimulation potential of said first electrode is reduced and sensing of an evoked response is enhanced;

sensing means, coupled to said ring electrode, for detecting said evoked response; and means for transmitting the detected evoked response to a point of use.

7. Apparatus as described in claim 6, including means for providing a charge dump signal; said discharging means comprising a FET and a resistor that is shorted by the FET in response to said charge dump signal to provide rapid discharge of said capacitor.

* * * * *